United States Patent [19]

Frazer

[11] Patent Number: Plant 7,634

[45] Date of Patent: Aug. 27, 1991

[54] AGLAONEMA PLANT NAMED 80-57

[75] Inventor: Edwin J. Frazer, P.O. Box 200, Brisbane, Queensland, Australia, 4069

[73] Assignee: Edwin J. Frazer, Kenmore, Australia

[21] Appl. No.: 515,105

[22] Filed: Apr. 27, 1990

[51] Int. Cl.[5] ..... A01H 5/00

[52] U.S. Cl. ..... Plt./88

[58] Field of Search ..... Plt./88

*Primary Examiner*—James R. Feyrer

*Attorney, Agent, or Firm*—Foley & Lardner

[57] ABSTRACT

An Aglaonema plant named 80-57, chracterized by its relatively small, narrow leaves, excellent branching habit, and its tricolored upper leaf surface in which the dark background color and the relatively light secondary color provide a distinct contrast.

1 Drawing Sheet

The present invention comprises a new and distinct cultivar of *Aglaonema hybrida* known by the cultivar name 80-57.

The new cultivar is a product of a planned breeding program carried out by the invention Edwin J. Frazer, P.O. Box 200, Kenmore, Queensland, Australia 4069. The female parent was the Aglaonema cultivar named Manilla and the pollen parent was an unnamed *Aglaonema commutatum* Treubii. The cultivar was discovered from the progeny of the stated cross by Edwin J. Frazer. Asexual propagation by division and tissue culture was used to increase the number of plants for evaluation, and has demonstrated the stability of the combination of characteristics of the new cultivar from generation to generation.

The following observations, measurements and values describe plants grown in Palmdale, Fla., under greenhouse conditions which closely approximate those generally used in horticultural practice.

The following traits have been repeatedly observed and are determined to be basic characteristics of 80-57, which in combination distinguish 80-57 from other Aglaonema of the same general type. The characteristics are described by reference to the well known commercial cultivars Silver Queen and Maria, the closest comparision cultivars.

1. 80-57 has smaller and narrower leaves than both Silver Queen and Maria.

2. 80-57 branches more freely than both Silver Queen and Maria.

3. The leaf color of 80-57 is darker than Silver Queen and Maria.

4. The tricolored leaves provide a very pleasant visual appearance.

The accompanying color photograph comprises a front view of a typical plant of 80-57, grown in a six inch pot. Colors are depicted as accurately as possible with color illustrations of this type.

All color references are to The Royal Horticultural Society Colour Chart. Color values are as close as possible, but color will vary depending on horticultural practices such as temperature, light conditions and fertilization rate, among others.

Origin: Seedling.

Classification: *Aglaonema hybrida* cv. 80-57.

Propagation: Asexual reproduction either by tissue culture or division.

Plant: In a 6 inch pot, 80-57 has a height of approximately 14 cm. to 17 cm. from the soil surface to the junction of the petioles of the last two (2) unrolled leaves, and is approximately 37 cm. to 43 cm. in width after approximately 48 weeks to 54 weeks under appropriate growing conditions from division. All measurements are based on the above parameters.

Stem:

*Growth pattern.*—The stem is erect in growth and is approximately 1.0 cm to 1.5 cm. in diameter five (5) cm. above the soil surface. Internode distance is approximately 5 mm. to 7 mm. three (3) cm. above the soil.

*Color.*—The stem is 191A blotched with 139A.

Petiole: The following information is based on the fourth expanded leaf from the apex.

Growth pattern.—The petiole has fleshy edges extending from the midrib which will be referred to as wings. The wings are approximately 3 mm. to 5 mm. wide at the midpoint of the wing, and extend from the base of the petiole to within approximately 7 cm. to 9 cm. of the leaf base. The apex of the wings is acute. The petiole follows the stem axis but diverges from the axis approximately 1 cm. to 2 cm. from the leaf base, forming a horizontal distance from the edge of the stem to the leaf base of approximately 5 cm to 6 cm.

*Physical dimensions.*—The petiole is straight from its base to the apex of the wing tip and bends away from the stem. The petiole is approximately 3 mm. to 5 mm. in diameter one-half (½) way between the top of the wing and the base of the leaf. The petiole is approximately 11 cm. to 15 cm. in length.

*Color.*—The petiole ranges in color from 137A to 191C, and the petiole wings are somewhat lighter.

Leaf:

*Growth pattern.*—The leaf is ovate with an acuminate apex and a cordate base. The margin is entire. The leaf is asymmetric, with the side of the leaf unrolling first having less surface area and fewer undulations on the leaf margin than the side unrolling last. The leaf is oriented parallel to the stem axis at the time of full unrolling, changing to perpendicular to the stem axis as more leaves unroll above it. The midrib is flat over the length of the leaf. The leaf blade droops near the margin.

*Physical dimensions.*—For the pot size and growing time indicated, an average sized leaf is approximately 20 cm. to 26 cm. long and approximately 5 cm. to approximately 7 cm. wide. The leaf is moderately thick.

*Midrib.*—The midrib is thick and 137A in color on the upper surface and 191A in color on the lower surface.

*Primary veins.*—The primary veins are sunken into the upper side and protrude out of the lower side. The primary veins are the same color as the leaf tissue surrounding them.

*Color and pattern.*—The leaf is tricolor on the upper side, with the darker outer areas or background being in the range of 139A to 136A. The lightest areas are irregularly shaped with their bases terminating at the midrib, and are 191C in color. There are irregular blotches of a third color 189A primarily at the borders of the two main colors. The lower side of the leaf is bicolor with the darker outer background areas being 191A, with axially spaced and alternate lighter flame-like areas extending out from the midrib being 139A.

Axillary breaks: There is approximately 4 to 6 axillary breaks, with at least one (1) leaf expanded. Leaves will show true color and pattern by the first leaf.

Inflorescence: Not commercially significant.

Roots: Thick white roots with finer laterals.

General observations: Aglaonema 80-57 is a narrow leaved, high branching, fast growing Aglaonema. The number of branches and the horizontal position of the leaves make the plant appear dense. The silver areas on a dark green background add to the visual display.

I claim:

1. A new and distinct Aglaonema plant named 80-57, as described and illustrated.

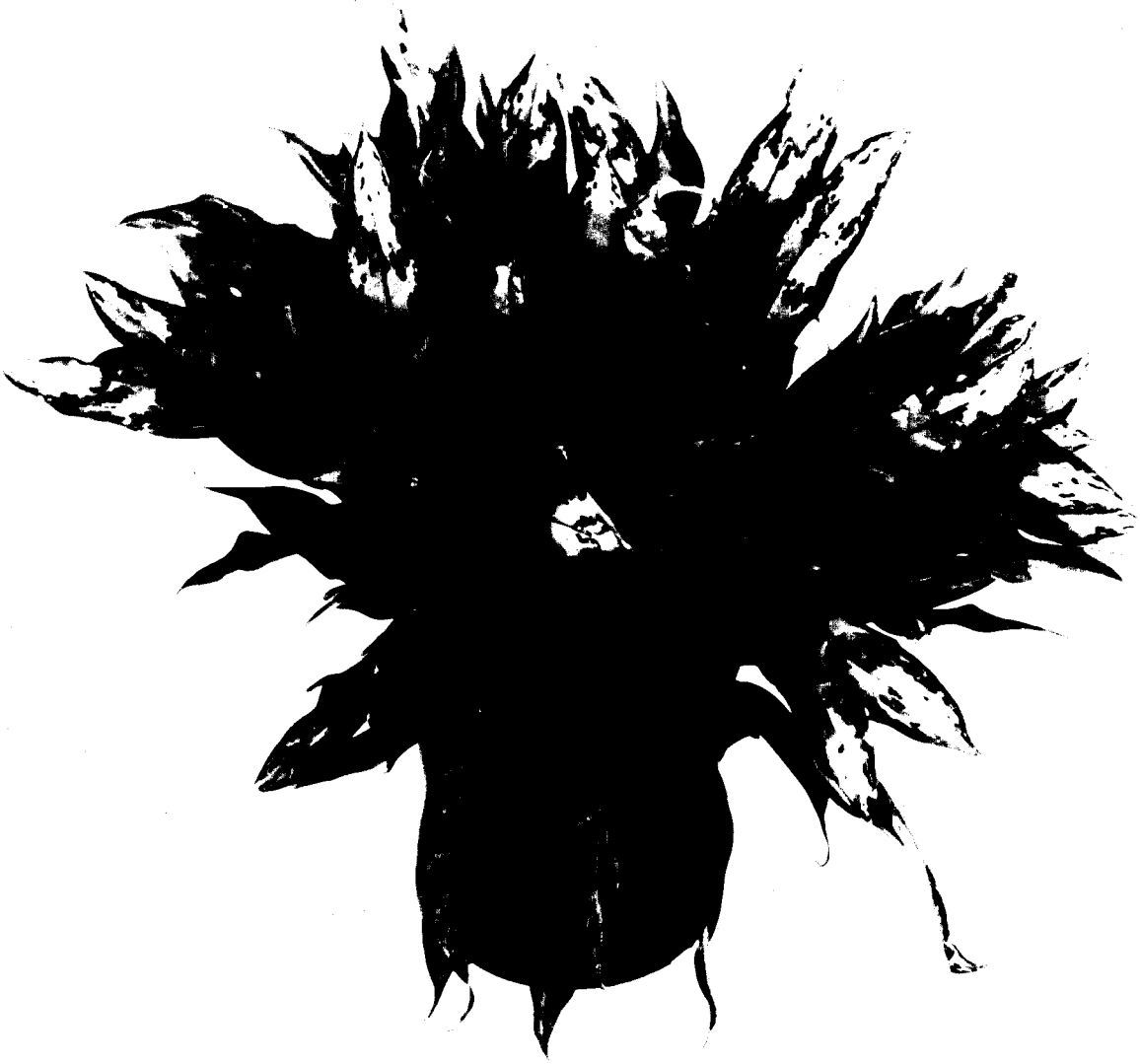

* * * * *